United States Patent [19]

Albrecht et al.

[11] Patent Number: 4,912,214

[45] Date of Patent: Mar. 27, 1990

[54] ISOTHIAZOLYL BETA-LACTAM ANTIBACTERIAL AGENTS

[75] Inventors: Harry A. Albrecht, Towaco; Dennis D. Keith, Montclair; Frederick M. Konzelman, West Paterson, all of N.J.

[73] Assignee: Hoffman-La Roche Inc., Nutley, N.J.

[21] Appl. No.: 378,685

[22] Filed: Jul. 11, 1989

Related U.S. Application Data

[63] Continuation of Ser. No. 193,390, May 12, 1988, abandoned, which is a continuation of Ser. No. 793,603, Oct. 31, 1985, abandoned.

[51] Int. Cl.[4] ............... A61K 31/425; C07D 417/14; C07D 417/12
[52] U.S. Cl. ................................ 540/363; 540/364
[58] Field of Search ........................ 540/363, 364

[56] References Cited

U.S. PATENT DOCUMENTS 4,587,047  5/1986  Breuer ........................ 544/295

Primary Examiner—Mark L. Berch
Attorney, Agent, or Firm—George M. Gould; Bernard S. Leon; A. Kate Huffman

[57] ABSTRACT

Compounds of the formula

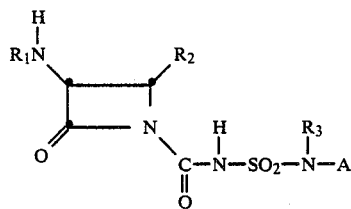

wherein A is

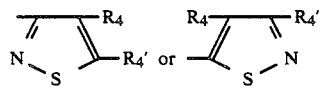

in which $R_1$ is acyl, $R_2$ is hydrogen, lower alkyl, lower alkoxy-carbonyl or aminocarbonyl, $R_3$ is hydrogen or lower alkyl, $R_4$ and $R_4{'}$ are each hydrogen, lower alkyl, lower alkoxy, aryl, aryloxy or aralkyl, as well as the pharmaceutically acceptable salts of such compounds, are useful as antibacterial agents for combatting infections in mammals.

30 Claims, No Drawings

ISOTHIAZOLYL BETA-LACTAM ANTIBACTERIAL AGENTS

This application is a continuation of application Ser. No. 193,390, filed May 12, 1988 now abandoned, which is a continuation of Ser. No. 793,603, filed Oct. 31, 1985, now abandoned.

RELATED CASES

This application is related to Ser. No. 615,607, filed May 31, 1984 now abandoned, in the names of Harry Allan Albrecht, Frederick Martin Konzelmann and Dennis Dalton Keith.

SUMMARY OF THE INVENTION

The novel family of $\beta$-lactam antibacterials of the present invention encomoasses compounds of the formula $$\underset{H}{R_1N} \quad R_2 \quad \text{-- I}$$
[structure showing β-lactam ring with N—C(=O)—N—SO$_2$—N(R$_3$)—A substituent]

wherein A is

[isothiazolyl structures with R$_4$, R$_4'$ substituents]

$R_1$ is acyl, $R_2$ is hydrogen, lower alkyl, lower alkoxycarbonyl or aminocarbonyl, $R_3$ is hydrogen, and lower alkyl, and $R_4$ and $R_4'$ are each hydrogen, lower alkyl, which may be substituted, lower alkoxy which may be substituted, aryl, substituted aryl, aryloxy, substituted aryloxy or aralkyl.

DETAILED DESCRIPTION OF THE INVENTION

Exemplary substituents to be substituted on other radicals, include, cyano, amino, lower alkyl lower alkoxy, mercapto, lower alkylthio and the like.

The invention is also considered to encompass pharmaceutically acceptable salts of compounds of the formula I. Examples of salts provided by the present invention are salts with bases; for example alkali metal salts such as the sodium salt and the potassium salt, the ammonium salt, alkaline earth metal salts such as the calcium salt, salts with organic bases such as salts with amines (e.g. salts with N-ethylpiperidine procaine dibenzylamine N,N'-dibenzylethylethylenediamine, alkylamines or dialkylamines) and salts with amino acids (e.g. salts with arginine or lysine).

As used in this specification, the term "lower alkyl" or "alkyl" refers to both straight and branched chain saturated hydrocarbon groups having 1 to 8 and preferably, 1 to 4 carbon atoms, which may or may not be substituted, such as, for example, methyl, ethyl, propyl, isopropyl tertiary butyl, halomethyl such as chloromethyl or bromomethyl and the like.

As used herein, the term "aralkyl" refers to groups comprising a lower-alkyl residue substituted by one or more aryl or substituted aryl groups, such as, for example phenylmethyl, phenylethyl, phenylpropyl, phenylisopropyl, phenyl-tertiary butyl hydroxyphenyl methyl and the like.

As used herein, the term "aryl" or "ar" as in aralkyl for example, refers to a carbocyclic aromatic group, which can be substituted or unsubstituted, such as, for example, phenyl, hydroxyphenyl, tolyl, chlorophenyl and the like.

The term "halo" as used herein represents all four forms thereof, i.e. chloro, bromo, iodo or fluoro unless otherwise specified.

As used herein the term "lower alkoxy" refers to substituted or unsubstituted alkoxy groups wherein the "alkyl" portion is a lower alkyl group as defined hereinbefore. Exemplary are methoxy, ethoxy, propoxy and the like.

The term "acyl", as used herein means and includes all organic radicals derived from an organic acid (i.e., a carboxylic acid) by removal of the hydroxyl group. Although the group $R^1$ may be any one of many acyl radicals, certain acyl groups are preferred.

Exemplary acyl groups are those acyl groups which have been used in the past to acylate $\beta$-lactam antibiotics including 6-aminopenicillanic acid and derivatives and 7-aminocephalosporanic acid and derivatives; see, for example, Cephalosporins and Penicillins, edited by Flynn, Academic press (1972), Belgian Pat. No. 866,038 published Oct. 17, 1978, Belgian Pat. No. 867,994, published Dec. 11, 1978, U.S. Pat. No. 4,152,432, issued May 1, 1979, U.S. Pat. No. 3,971,778, issued July 27, 1976, and U.S. Pat. No. 4,172,199, issued Oct. 23, 1979. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula $$R^5-\overset{O}{\underset{\|}{C}}-$$

wherein $R^5$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethyllthio groups.

(b) Carbocyclic aromatic groups having the formula

[three benzene ring structures with R$^6$, R$^7$, R$^8$ substituents and side chains: —(CH$_2$)$_n$—C(=O)—, —CH(R$^9$)—C(=O)—, and —CH$_2$—O—C(=O)—]

-continued

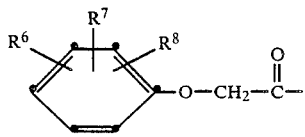

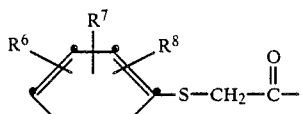

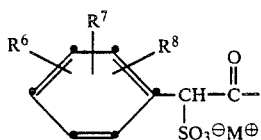

or

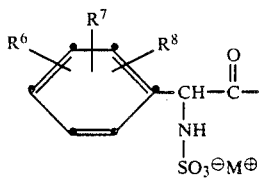

wherein n is 0, 1, 2 or 3; $R^6$, $R^7$, and $R^8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R^9$ is amino, hydroxyl a carboxyl salt, protected carboxy such as benzyloxycarbonyl, formyloxy, a sulfo salt, such as a sodium salt, a potassium salt or an amine salt, a sulfoamino salt, such as a sodium salt, a potassium salt or an amine salt or azido.

Preferred carbocyclic aromatic acyl groups include those having the formula

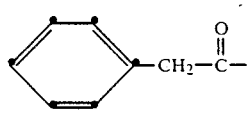

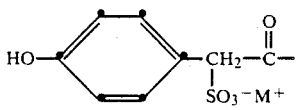

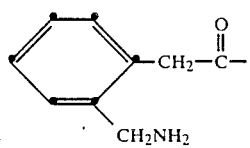

and

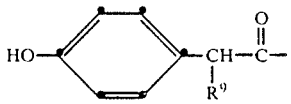

($R^9$ is preferably an amino group, a hydroxy group, or a carboxyl salt or sulfo salt)

Examples of other acyl groups of the formula

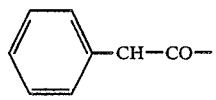

suitable for the purposes of the present invention are α-sulfophenyl-acetyl, α-hydroxysulfonyloxyphenylacetyl, α-sulfamoylphenylacetyl, α-(phenoxycarbonyl)-phenyl-acetyl, α-(p-tolyloxycarbonyl)phenylacetyl, α-formyloxyphenylacetyl, α-carboxyphenylacetyl, α-benzyloxycarbonylphenylacetyl, 2-(N,N-dimethylsulfamoyl)-2-phenylacetyl 2-bromo-2-thienylacetyl, etc.

(c) Heteroaromatic groups having the formula

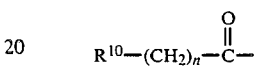

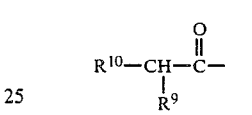

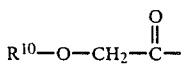

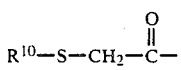

or

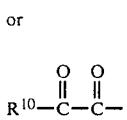

wherein n is 0, 1, 2 or 3; $R^9$ is as defined above; and $R^{10}$ is a substituted or unsubstituted 5- 6- or 7-membered heterocyclic ring containing 1, 2, 3 or 4 (preferably 1 or nitrogen oxygen or sulfur atoms. Exemplary heterocyclic rings are thienyl, furyl pyrrolyl, pyridinyl, pyrazinyl, thiazolyl, pyrimidinyl and tetrazolyl. Exemplary substituents are halogen, hydroxyl, nitro, amine, cyano, trifluoromethyl alkyl of 1 to 4 carbon atoms or alkoxy of to 4 carbon atoms.

Preferred heteroaromatic acyl groups include those groups of the above formulas wherein $R^{10}$ is 2-amino-4-thiazolyl, 2-amino-5-halo-4-thiazolyl, 4-aminopyrimidin-2-yl, 2-amino-1,3,4-thiadiazol-5-yl, 2-thienyl or 2-furanyl.

(d) [[(4-Substituted-2 3-dioxo-1-piperazinyl)-carbonyl]-amino]arylacetyl groups having the formula

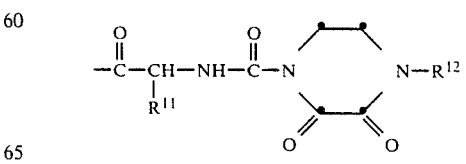

wherein $R^{11}$ is an aromatic group (including carbocyclic aromatics such as those of the formula

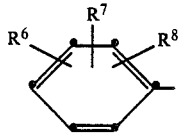

wherein $R^6$, $R^7$, and are as previously defined and heteroaromatics as included within the definition of $R^{10}$); and $R^{12}$ is alkyl, substituted alkyl (wherein the alkyl group is substituted with one or more halogen, cyano, nitro, amino or mercapto groups) e.g. 4-lower alkyl (preferably ethyl or methyl) -2, 3-dioxo-1-piperazinecarbonyl-D-phenylglycyl.

(e) (Substituted oxyimino) arylacetyl groups having the formula

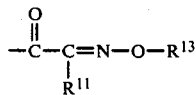

herein $R^{11}$ is as defined above and $R^{13}$ is hydrogen lower alkyl and $C_3$–$C_7$ cycloalkyl or substituted lower alkyl (wherein the alkyl group is substituted with 1 or more halogen, cyano, nitro, amino, mercapto, lower alkylthio, aromatic group (as defined by $R^{11}$), carboxyl (including salts thereof), amido, lower alkoxycarbonyl, phenylmethoxycarbonyl, diphenylmethoxycarbonyl, hydroxyalkoxyphosphinyl, dihydroxyphosphinyl, hydroxy (phenylmethoxy) phosphinyl, or diloweralkoxyphosphinyl substituents).

Examples of

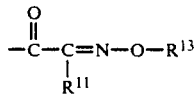

grouping are
2-[(2-chloroacetamidothiazol-4-yl)-2-[(p-nitrobenzyloxycarbonyl]methoxyimino]acetyl
2-(2-chloroacetamidothiazol-4-yl)-2-methoxyiminoacetyl,
2-(2-aminothiazol-4-yl)-2-isopropoxy-iminoacetyl,
2-(2-aminothiazol-4-yl)-2-methoxyiminoacetyl,
2-(2-aminothiazol-4-yl)-2-oxyiminoacetyl,
2-thienyl-2-methoxyiminoacetyl,
2-furyl-2-methoxyiminoacetyl,
2-(4-hydroxyphenyl)-2-methoxyiminoacetyl,
2-phenyl-2-methoxy-iminoacetyl, 2-phenyl-2-oxyiminoacetyl,
2-thienyl-2-oxyiminoacetyl,
2-thienyl-2-(dichloroacetyloxyimino) acetyl, 2-[4-(γ-D-glutamyloxy)phenyl]-2-oxyiminoacetyl,
2-[4-(3-amino-3-carboxypropoxy)phenyl]-2-oxyiminoacetyl,
2-(5-chloro-2-chloro-acetamidothiazol-4-yl)-2-methoxyiminoacetyl,
2-(5-chloro-2-aminothiazol-4-yl)-2-methoxyiminoacetyl,
2-[γ-(t-butoxy-carbonyl)isopropoxyimino]-2-(2-sulfoaminothiazol-4-yl)-acetyl,
2-γ-(t-butoxyoarbonyl)isopropoxyimino-2-(2-triphenylmethylamino-thiazol-4-yl)acetyl,
2-(2-chloroacetamidothiazol-4-yl)-2-isopropoxyiminoacetyl,
2-methoxyimino-2-(2-sulfoaminothiazol-4-yl)acetyl,
2-[(2-aminothiazol-4-yl)-2-carboxymethoxy imino]acetyl
2-[2-(2-mesylaminothiazol-4-yl)-2-isopropoxyiminoacetyl,
2-(2-imino-3-mesyl-4-thiazolin-4-yl)-2-isopropoxyiminoacetyl,
2-[(2-Aminothiazol-4-yl)-2-(carboxyisopropoxyimino acetyl etc.

(f) (Acylamino) arylacetyl groups having the formula

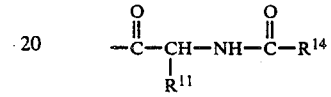

wherein $R^{11}$ is as defined above and $R^{14}$ is

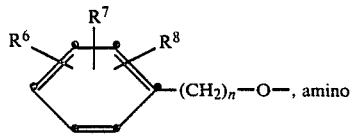

alkylamino, (cyanoalkyl) amino, or acylamino.

Preferred (acylamino) arylacetyl groups of the above formula include those groups wherein $R^{14}$ is amino, or acylamino. Also preferred are those groups wherein $R^{11}$ is phenyl or 2-thienyl.

(g) [[[3-Substituted-2-oxo-1-imidazolidinyl]carbonyl]amino] arylacetyl groups having the formula

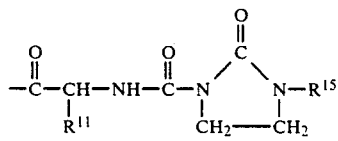

wherein $R^{11}$ is as defined above and $R^{15}$ is hydrogen, alkylsulfonyl, arylmethyleneamino (i.e., —N=CH—$R^{11}$ wherein $R^{11}$ is as defined above),

(wherein $R^{16}$ is hydrogen, alkyl or halogen substituted alkyl), aromatic group (as defined by $R^{11}$ above), alkyl or substituted alkyl (wherein the alkyl group is substituted with one or more halogen, cyano, nitro, amino or mercapto groups).

Preferred [[[3-substituted-2-oxo-1-imidazolidinyl]carbonyl]amino]arylacetyl groups of the above formula include those wherein $R^{11}$ is phenyl or 2-thienyl. Also preferred are those groups wherein $R^{15}$ is hydrogen, methylsulfonyl, phenylmethyleneamino or 2-furylmethyleneamino.

Especially preferred are compounds of the formula

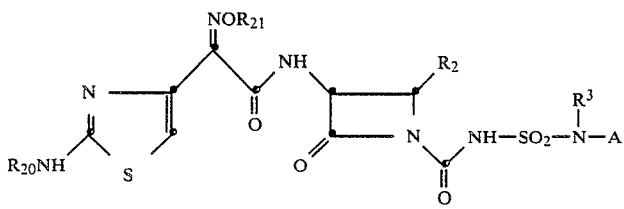

II where A is

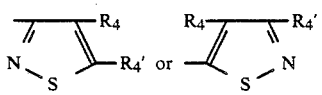

wherein $R_2$, $R_3$, $R_4$, and $R_4'$ are as previously defined, $R_{20}$ is hydrogen or an amino protecting group such as trityl or chloroacetyl, $R_{21}$ is hydrogen, lower alkyl, or a group of the formula

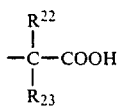

wherein $R_{22}$ and $R_{23}$ are selected from the group consisting of hydrogen and lower alkyl, or $R_{22}$ and $R_{23}$ taken together with the carbon atom to which they are attached form a $C_3$ to $C_7$ carbocylic ring, e.g., cyclopropyl, cyclobutyl or cyclopentyl. Still more preferred are compounds of the formula II in which $R_2$, $R_3$, $R_4$, and $R_4'$ are each hydrogen or methyl, $R_{20}$ is hydrogen, and $R_{21}$ is methyl or a group of the formula

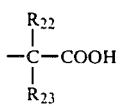

wherein $R_{22}$ and $R_{23}$ are each either hydrogen or methyl.

It will be observed that compounds of formula I have a chiral center at the position 3 carbon atom of the β-lactam ring. In compounds encompassed by the invention, the stereo configuration of the position 3 chiral carbon atoms is the same as that of the position 6 carbon atom in naturally occurring penicillins such as penicillin G, and of the position 7 carbon atom in naturally occurring cephalosporins, such as cephalosporin C. Pursuant to convention, this stereo configuration of the position 3 carbon atom in compounds of formula I is designated the "S" configuration.

Mixtures of the S and R isomers of Compound I, such as racemic mixtures are also considered to be within the scope of the invention.

The group $R^2$, which is a substituent of the position 4 carbon atom, may be either cis or trans with respect to the acylamino group attached to the position 3 carbon atom β-lactam compounds according to the invention have activity against a broad spectrum of both gram-negative and gram-positive bacteria.

The compounds of this invention can be used as agents to combat bacterial infection (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular and as a suppository.

Compounds of Formula I can be prepared utilizing a known, starting material, having the formula

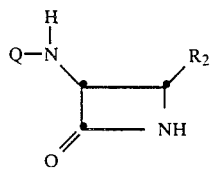

III or the formula

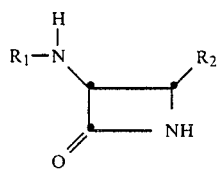

IV wherein Q is any known amino protecting group, such as, for example, benzyloxycarbonyl (CBZ) or tert-butyloxycarbonyl (t-BOC). and wherein $R^1$ and $R^2$ are the same as hereinbefore described.

Compounds of the formula I above are prepared in one process embodiment in two stages. In the first stage, a compound of the formula IV is reacted with a compound of the formula

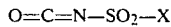

$O=C=N-SO_2-X$ wherein X is a leaving group e.g. a halogen such as chlorine. The first stage is suitably run in a dry inert organic solvent such as acetonitrile, methylene chloride, 1,2-dimethoxyethane, THF dioxane and the like.

A preferred compound for this purpose is chlorosulphonyl isocyanate. Suitably, this first stage is effected below room temperature i.e., in the cold, suitably at $-70°$ C. to about $10°$ C. preferably from about $-55°$ C. to about $0°$ C.

The second stage occurs by adding to the reaction medium upon completion of the first stage, a compound of the formula

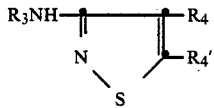

or a compound of the formula

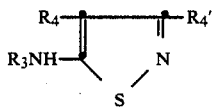

wherein $R_3$, $R_4$ and $R_4'$, are as above, together with a suitable tertiary amine or amines, such as triethylamine and pyridine. The two-stage reaction is conducted under anhydrous conditions, preferably under an inert gas such as argon.

It should be understood that if it is desired to prepare a compound of the formula I above which contains a functional group such as a hydroxyl group or an amino radical present in the $R_1$ acyl chain which would react under the conditions utilized in the condensation of an isocyanate, such functional groups must be protected, in a manner known in the art, using suitable protecting groups such as t-BOC, CBZ, trityl or chloroacetyl. Such protecting groups are removed in a subsequent step or steps to give the desired compound of formula I. Alternatively, a compound of the formula III can be used as starting material. That is to say, the compound of the formula III which bears a protecting group is first utilized for the two-stage reaction. The protecting group is then removed giving $R_1$ as hydrogen and the desired acyl group is introduced to obtain the desired compound of the formula I according to procedures well known in the art.

The Examples which follow further illustrate the invention in more detail, but are not intended to limit its extent. In the Examples all temperatures are given in degrees Centigrade, unless otherwise stated.

The following compounds are prepared by procedures analogous to those above by routine variations in accordance with accepted chemical procedure and practices. For example, acylation reactions are accomplished optionally either with the appropriate acid chloride or by other methods known in the art, such as reaction with the appropriate acid, dicyclohexylcarbodiimide, and N-hydroxy-benzotriazole. Procedures are subject also to the use, where necessary, of protecting groups e.g. trityl or t-Boc to protect amino functions) according to techniques well known in the art.

EXAMPLE 1

(S)-1-[[[[[(5-Methyl-3-isothiazolyl)amino]sulfonyl]amino]carbonyl]-2-oxo-3-azetidinyl]carbamic acid 1,1-dimethylethyl ester Under an argon atmosphere, a stirred mixture of 520 mg (2.8 mmol) of (S)-(2-oxo-3-azetidinyl)carbamic acid 1,1-dimethylethyl ester and 16 mL of dry 1,2-dimethoxyethane was cooled to $-50°$, and a solution 476 mg (3.36 mmol) of chlorosulfonyl isocyanate in 2 mL of 1,2-dimethoxyethane was added. The reaction mixture was allowed to warm to $-30°$ C. for ten minutes, and then cooled again to $-50°$ C. while a solution of 274 mg (3.36 mmol) of 5-methyl-3-isothiazoamine, 1.24 mL of triethylamine, and 0.92 mL of dry pyridine in 2 mL of 1,2-dimethoxyethane was added. The mixture was allowed to warm to $0°$ C. and stirred at that temperature for 2 hours. The solvent was evaporated under reduced pressure; methylene chloride was added and the evaporation repeated. The residue was dissolved in ethyl acetate and water, and the mixture adjusted to pH3 by addition of hydrochloric acid. The organic phase was washed with brine dried ($Na_2SO_4$), decolorized with charcoal and concentrated under reduced pressure to obtain 800 mg of the title compound.

EXAMPLE 2

(S)-3-Amino-N-[[(5-methyl-3-isothiazolyl)amino]sulfonyl]-2-oxo-1-azetidinecarboxamide trifluoracetic acid salt A mixture of 1.5 mL of trifluoroacetic acid and 0.3 mL of anisole was cooled to $0°$, and 198 mg (0.49 mmol) of (S)-1-[[[[[(5-methyl-3-isothiazolyl)amino]sulfonyl]amino]carbonyl]-2-oxo-3-azetidinyl]carbamic acid 1,1-dimethylethyl ester was added. The mixture was stirred at $0°$ (for 3 hours, and concentrated under reduced pressure. Methylene chloride was added, and evaporation to dryness was repeated twice. The residue was triturated with ether to obtain 160 mg of the title compound as a white solid.

EXAMPLE 3

(S,Z)-2-[(Chloroacetyl)amino]-α-(methoxyimino)-N-[1-[[[[(5-methyl-3-isothiazolyl)amino]sulfonyl]amino]carbonyl]-2-oxo-3-azetidinyl]thiazole-4-acetamide A solution of 436 mg (4.32 mmol) of triethylamine in 3.2 mL of dry DMF was cooled to $-8°$ C. and 502 mg (1.2 mmol) of (S)-3-amino-N-[[(5-methyl-3-isothiazolyl)amino]sulfonyl]-2-oxo-1-azetidinecarboxamide trifluoroacetic acid salt was added. To the resulting solution was added dropwise a solution of 520 mg (1.2 mmol) of (Z)-[2-(chloroacetyl)amino-4-thiazolyl](methoxyimino)acetyl chloride hydrochloride in 4 mL of chloroform. The mixture was stirred cold for 15 minutes and at room temperature for three hours before concentrating under reduced pressure. Methylene chloride was added to the residue, and evaporation under reduced pressure was repeated. The residue was taken up in ethyl acetate and water, and the mixture adjusted to pH3 with N hydrochloric acid. The organic phase was washed with brine, dried ($Na_2SO_4$), decolorized with charcoal, and concentrated under reduced pressure to obtain 420 mg of the title compound.

EXAMPLE 4

(S,Z)-2-Amino-α-(methoxyimino)-N-[1-[[[[(5-methyl-3-isothiazolyl)amino]sulfonyl]amino]carbonyl]-2-oxo-3-azetidinyl]thiazole-4-acetamide sodium salt To a solution of 383 mg (0.7 mmol) of (S,Z)-2-[(chloroacetyl)amino)-α-methoxyimino)-N-[1-[[[[(5-methyl-3-isothiazolyl)amino]sulfonyl]amino]carbonyl]-2-oxo-3azetidinyl]thiazole-4-acetamide in 8.6 mL of DMF at $0°$ C. was added 281 mg (1.91 mmol) of N-methyldithiocarbamic acid sodium salt hydrate. The mixture was stirred cold for 10 minutes and at room temperature for three hours, before concentrating under reduced pressure. Evaporation under reduced pressure was repeated twice more after addition of 10 mL portions of methylene chloride. The residue was triturated with ethanol to obtain a solid. This was dissolved in water, and the solution decolorized with charcoal and freeze-dried to yield 157 mg of product. After further purification by $C^{18}$ reverse-phase HPLC, using a water-methanol gradient, the title compound was obtained: NMR (Me$_2$SO-d$_6$) δ 2.47 (s, 3H, isothiazole Me), 3.32 (H$_2$O peak, obscures multiplet of 4β H), 3.66 (t, J$_{4\alpha, 4\beta}$=J$_{3,4\alpha}$=6 Hz, 1H, CHC̲H̲ Hβ), 3.85 (s, 3H, OMe̲), 4.85 (m, 1H, NHC̲H̲CH$_2$), 6.73 (s, 1H, isothiazole H̲), 6.95 (s, 1H, thiazole H̲), 7.21 (s, 2H, NH$_2$), 8.97 (s, 1H, NH), 9.12 (d, J=8 Hz, 1H, CONH); IR (KBr) 3420, 3320, 1778, 1730, 1663, 1620 cm$^{-1}$.

EXAMPLE 5

(S)-N-[1-[[[[(5-Methyl-3-isothiazolyl)amino]sulfonyl]amino]carbonyl]-2-oxo-3-azetidinyl]benzeneacetamide is prepared following the procedure of Example 3.

EXAMPLE 6

S-[1-[[[[(5-Methyl-3-isothiazolyl)amino]sulfonyl]amino]carbony 1]-2-oxo-3-azetidinyl]carbamic acid phenylmethyl ester is prepared following the procedure of Example 3.

EXAMPLE 7

[3S-trans;(Z)]-α-(Methoxyimino)-N-[4-methyl-2-oxo-3-azetidinyl]-2-[(triphenylmethyl)amino]thiazole-4-acetamide A mixture of 936 mg (0.004 mol) of (3S-trans)-(4-methyl-2-oxo-3-azetidinyl)carbamic acid phenylmethyl ester, 50 mL of methanol, and 270 mg of 10% palladium on carbon catalyst was hydrogenated (5 minutes) on a Parr apparatus at an initial gauge pressure of 50 psi. After filtration of the catalyst, the solution was concentrated to dryness under reduced pressure. The residual [3S-trans)-3-amino-4-methyl-2-azetidinone was dissolved in 2 mL of DMF and added to a stirred mixture of 1.7 g (0.004 mol) (Z)-methoxyimino-2-[(triphenylmethyl)amino]thiazole-4-acetic acid, 20 mL of DMF, 540 mg (0.004 mol) of 1-hydroxybenzotriazole, and 824 mg (0.004 mol) N,N'-dicyclohexylcarbodiimide. The mixture was stirred 4 hours, diluted with 200 mL of water and adjusted to pH 7.5 with aqueous NaHCO$_3$. The mixture was extracted with three 300 mL portions of ethyl acetate and the combined extracts washed with water and brine, dried (Na$_2$SO$_4$), and decolorized with charcoal. The amorphous solid obtained by evaporation of the solvent was purified by MPLC on a Waters Prep 500 using 4:1 ethyl acetate-hexane, to obtain 1.2 g of product.

EXAMPLE 8

[3S-trans;(Z)]-2-Amino-α-(methoxyimino)-N-[4-methyl-1-[[[[(5-methyl-3-isothiazolyl)amino]sulfonyl]amino ]carbonyl]-2-oxo-3-azetidinyl]thiazole-4-acetamide Sodium Salt is prepared utilizing the intermediate prepared in Example 7 following the procedures of Examples 1 and 2.

EXAMPLE 9

(S,Z)-α-[[2-(1,1-dimethylethoxy)-1,1-dimethyl-2-oxoethoxy]imino]-N-(2-oxo-3-azetidinyl)-2-[(triphenylmethyl)amino]-4-thiazoleacetamide A mixture of 2.20 g (0.01 mmol) of (S)-(2-oxo-3-azetidinyl) carbamic acid phenylmethyl ester, 125 mL of methanol, and 0.68 g of 10% palladium on carbon catalyst was hydrogenated (5 minutes) on a parr apparatus at an initial gauge pressure of 50 psi. After filtration of the catalyst, the solution was concentrated to dryness under reduced pressure. The residual (S)-3-amino-2-azetidinone was dissolved in 10 mL of DMF and added to a mixture of 5.71 g (0.01 mol) of (Z)-α-[[2-(1,1-dimethylethoxy)-1,1-dimethyl-2-oxoethoxy]imino]-2-[(triphenylmethyl)amino]-4-thiazole acetic acid, 40 mL of DMF, 2.06 g (0.01 mol) of N,N'-dicyclo-hexylcarbodiimide and 1.35 g (0.01 mol) of 1-hydroxybenzo-triazole. The mixture was stirred for 4 hours, diluted with 500 mL of water and adjusted to pH 7.5 with aqueous NaHCO$_3$. The mixture was extracted with four 300 mL portions of ethyl acetate. The combined extracts were washed with water and brine, dried (Na$_2$SO$_4$), decolorized with charcoal and concentrated to dryness. After purification by HPLC on a Waters Prep 500, using 4:1 ethyl acetate-hexane, 3.8 g of (S,Z)-α-[[2-(1,1-dimethylethoxy)-1,1-dimethyl-2-oxoethoxy]imino]-N-(2-oxo-3-azetidinyl)-2-[(triphenylmethyl)amino]-4-thiazoleacetamide was obtained.

EXAMPLE 10

(S,Z)-2-[[[1-(2-Amino-4-thiazolyl)-2-[1-[[[[(5-methyl-3-isothiazolyl)amino]sulfonyl]amino]carbonyl]-2-oxo-3-azetidinyl]amino-2-oxoethylidene]imino]oxy]-2-methylpropanoic acid dipotassium salt is prepared from the intermediate of Example 9 following the procedure of Examples 1 and 2.

EXAMPLE 11

By the general procedure in Example 3, there is additionally prepared (S)-N-[1-[[[[(5-Methyl-3-isothiazolyl)amino]-sulfonyl]amino]carbonyl]-2-oxo-3-azetidinyl]-thiophene-2-acetamide.

EXAMPLE 12

By the general procedure in Example 3, there is additionally prepared (S)-N-[1-[[[[(5-Methyl-3-isothiazolyl)amino]sulfonyl]amino]carbonyl]-2-oxo-3-azetidinyl]-tetrazole-1-acetamide.

EXAMPLE 13

By the general procedure in Example 3, there is additionally prepared (S)-3-(2,6-Dichlorophenyl)-5-methyl-N-[1-[[[[(5-methyl-3-isothiazolyl)amino]sulfonyl]-amino]carbonyl]-2-oxo 3-azetidinyl]isoxazole-4-carboxamide.

EXAMPLE 14

By the general procedure described in Examples 1-4, there is additionally prepared (S)-2-aminomethyl-N-[1-[[[[(5-methyl 3-isothiazolyl)amino]sulfonyl]amino]carbonyl]-2-oxo-3 -azetidinyl]benzeneacetamide.

EXAMPLE 15

By the general procedure described in Example 3, there is additionally prepared (S)-α-cyano-N-[1-[[[[(5-methyl-3-isothiazolyl)amino]sulfonyl]amino]carbonyl]-2-oxo-3-azetidinyl]acetamide.

EXAMPLE 16

By the general procedure described in Example 3, there is additionally prepared (S)-α-[(cyanomethyl)-thio]-N-[1-[[[[(5-methyl-3-isothiazolyl)amino]sulfonyl]amino]carbonyl]-2-oxo-3-azetidinyl]acetamide.

EXAMPLE 17

By the general procedure described in Example 3, there is additionally prepared [3S-(3β),(R*)]-α-[[(2,3-dioxo-4-ethyl-1-piperazinyl)carbonyl]amino]-N-[1-[[[[(5-methyl-3-isothiazolyl)amino]sulfonyl]amino]carbonyl]-2-oxo-3-azetidinyl]propanamide.

EXAMPLE 18

By the general procedure described in Example 3, there is additionally prepared [3S-(3β),(R*)]-α-[[(2,3-dioxo-4-ethyl-1-piperazinyl)carbonyl]amino]-N-[1-[[[[(5-methyl-3-isothiazolyl)amino]sulfonyl]amino]carbonyl]-2-oxo-3-azetidinyl]benzeneacetamide.

EXAMPLE 19

By the general procedure described in Example 4, there is additionally prepared [3S-(3β),(R*)]-α-[[(2,3-dioxo-4-ethyl-1-piperazinyl)carbonyl]amino]-4-methoxy-N-[1-[[[[(5-methyl-3-isothiazolyl)amino]sulfonyl]amino]carbonyl]-2-oxo 3-azetidinyl]benzeneacetamide.

EXAMPLE 20

By the general procedures described in Example 4, there is additionally prepared [3S-(3β),(S*)]-α-[[(2,3-dioxo 4-ethyl-1-piperazinyl)carbonyl]amino]-N-[1-[[[[(5-methyl-3-isothiazolyl)amino]sulfonyl]amino]carbonyl]-2-oxo-3-azetidinyl]thiophene-2-acetamide.

EXAMPLE 21

By the general procedure described in Example 4, there is additionally prepared [3S-(3β),(S*)]-α-[[(2,3-dioxo-4-octyl-1-piperazinyl)carbonyl]-amino]-N-[1-[[[[(5-methyl-3-isothiazolyl)amino]sulfonyl]-amino]-carbonyl]-2-oxo-3-azetidinyl]thiophene-2-acetamide.

EXAMPLE 22

By the general procedure described in Example 4, there is additionally prepared [3S-(3β),(R*)]-α-[[(2,3-dioxo-4-octyl-1-piperazinyl)carbonyl]-amino]-N-[1-[[[[(5-methyl-3-isothiazolyl)amino]sulfonyl]-amino]carbonyl]-2-oxo-3-azetidinyl]benzeneacetamide.

EXAMPLE 23

By the general procedure described in Example 4, there is additionally prepared (S)-2-amino-N-[1-[[[[(5-methyl-3-isothiazolyl)amino]-sulfonyl]amino]carbonyl]-2-oxo-3-azetidinyl]thiazole-4-acetamide.

EXAMPLE 24

By the general procedure described in Example 3, there is additionally prepared (S,Z)-α-Methoxyimino-N-[1-[[[[(5-methyl-3-isothiazolyl)amino]sulfonyl]amino]carbonyl]-2-oxo-3-azetidinyl]benzeneacetamide.

EXAMPLE 25

By the general procedure described in Example 3, there is be additionally prepared (S,Z)-α-Methoxyimino-N-[1-[[[[(5-methyl-3-isothiazolyl)amino]sulfonyl]amino]carbonyl]-2-oxo-3-azetidinyl]thiophene-2-acetamide.

EXAMPLE 26

By the general procedure described in Example 3, there is additionally prepared [3S-(3β),(S*)]-α-[[[3-[2(Furylmethylene)amino]-2-oxo-1-imidazolidinyl]carbonyl]amino]-N-[1-[[[[(5-methyl-3-isothiazolyl)amino]sulfonyl]amino]carbonyl]-2-oxo-3-azetidinyl]thiophene-2-acetamide.

EXAMPLE 27

By the general procedure described above in Example 3, there is additionally prepared [3S-(3β),(R*)]-N-[-1-[[[[(5-methyl-3-isothiazolyl)amino]sulfonyl]amino]-carbonyl]-2-oxo-3-azetidinyl]-[[[3-[2-(thienylmethylene)amino]-2-oxo-1-imida-zolidinyl]carbonyl]amino]benzeneacetamide.

EXAMPLE 28

By the general procedure described in Examples 1–4, there is additionally prepared [3S-(3β),(R*)]-α-amino-N-[1-[[[[(5-methyl-3-isothiazolyl)amino]sulfonyl]amino]carbonyl]-2-oxo-3-azetidinyl]benzeneacetamide.

EXAMPLE 29

By the general procedure described in Examples 1–4, there is additionally prepared (3S)-α-[[[1-[[[[(5-Methyl-3-isothiazolyl)amino]sulfonyl]amino]carbonyl]-2-oxo-3-azetidinyl]-amino]carbonyl]benzeneacetic acid.

EXAMPLE 30

By the general procedure described in Examples 1–4, there is additionally prepared (S,Z)-5-Amino-α-ethoxyimino-N-[1-[[[[(5-methyl-3-isothiazolyl)amino]sulfonyl]amino]carbonyl]-2-oxo-3-azetidinyl]-1,2,4-thiadiazole-3-acetamide.

EXAMPLE 31

By the general procedure described in Examples 1–4, there is additionally prepared (S,Z)-[[[1-(2-Amino-4-thiazolyl)-2-[1-[[[[(5-methyl-3-isothiazolyl)amino]sulfonyl]amino]carbonyl]-2-oxo-3-azetidinyl]amino-2-oxoethylidene]imino]oxy]acetic acid.

EXAMPLE 32

By the general procedures described in Examples 1–4, there is additionally prepared (S,Z-2-[[[1-(2-Amino-4-thiazolyl)-2-[1-[[[[(3-methyl-5-isothiazolyl)amino]sulfonyl]amino]carbonyl]-2-oxo-3-azetidinyl]amino-2-oxoethylidene]imino]oxy]-2-methylpropanoic acid.

EXAMPLE 33

By the general procedures described in Examples 1–4, there is additionally prepared (S,Z)-2-Amino-α-(methoxyimino)-N-[1-[[[[(3-methyl-5-isothiazolyl)amino]sulfonyl]amino]carbonyl]-2-oxo-3-azetidinyl]-thiazole-4-acetamide.

EXAMPLE 34

By the general procedures described in Examples 1–4, there is additionally prepared (S,Z)-[[[1-(2-Amino-4-thiazolyl)-2-[1-[[[[(3-methyl-5-isothiazolyl)amino]sulfonyl]amino]carbonyl]-2-oxo-3-azetidinyl]amino-2-oxoethylidene]imino]oxy]acetic acid.

EXAMPLE 35

By the general procedures described in Examples 1–4, there is additionally prepared (S,Z)-2-Amino-N-[1-[[[[(3,4-dimethyl-5-isothiazolyl)amino]sulfonyl]amino]carbonyl]-2-oxo-3-azetidinyl]-α-(methoxyimino)-thiazole-4-acetamide.

EXAMPLE 36

By the general procedures described in Examples 1–4, there is additionally prepared (S,Z)-2-[[[1-(-2-Amino-4-thiazolyl)-2-[1-[[[[(3,4-dimethyl-5-isothiazolyl)amino]sulfonyl]amino]carbonyl]-2-oxo-3-azetidinyl]amino-2-oxoethylidene]imino]oxy]-2-methylpropanoic acid.

EXAMPLE 37

By the general procedures described in Examples 1–4, there is additionally prepared (S,Z)-[[[1-(2-Amino-4-thiazolyl)-2-[1-[[[[(3,4-dimethyl-5-isothiazolyl)amino]sulfonyl]amino]carbonyl]-2-oxo-3-azetidinyl]amino-2-oxoethylidene]imino]oxy]acetic acid.

EXAMPLE 38

By the general procedure described in Examples 1–4, there is additionally prepared [3S-(3β),(R*)]-α-Hydroxy-N-[1-[[[[(5-methyl-3-isothiazolyl)amino]sulfonyl]amino]carbonyl]-2-oxo-3-azetidinyl]benzeneacetamide.

EXAMPLE 39

By the general procedure described in Examples 1–4, there is additionally prepared [S-trans; (Z)]-2-[[[1-(2-Amino-4-thiazolyl)-2-[4-methyl-1-[[[[(5-methyl-3-isothiazolyl)amino]sulfonyl]amino]carbonyl]-2-oxo-3-azetidinyl]amino-2-oxoethylidene]imino]oxy]-2-methylpropanoic acid.

EXAMPLE 40

By the general procedure described in Examples 1–4, there is additionally prepared [S-trans; (Z)]-[[[1-(2-Amino-4-thiazolyl)-2-[4-methyl-1-[[[[(5-methyl-3-isothiazolyl)amino]sulfonyl]amino]carbonyl]-2-oxo-3-azetidinyl]amino-2-oxoethylidene]imino]oxy]acetic acid.

EXAMPLE 41

By the general procedure described in Examples 1–4, there is additionally prepared [3S-cis; (Z)]-2-Amino-N-[4-[[[(aminocarbonyl)]oxy]methyl]-1-[[[[(5-methyl-3-isothiazolyl)amino]sulfonyl]amino]carbonyl]-2-oxo-3-azetidinyl]-α-(methoxyimino)thiazole-4-acetamide.

EXAMPLE 42

By the general procedure described in Examples 1–4, there is additionally prepared (cis-rac)-3-[[[2-amino-α-(methoximino)-4-thiazolyl]acetyl]amino]-1-[[[[(5-methyl-3-isothiazolyl)amino]sulfonyl]amino]carbonyl]-4-oxoazetidine-2-carboxylic Acid Ethyl Ester.

EXAMPLE 43

By the general procedure described in Examples 1–4, there is additionally prepared (S,Z)-2-Amino-N-[1-[[[[(4-methoxy-5-methyl-3-isothiazolyl)amino]sulfonyl]amino]carbonyl]-2-oxo-3-azetidinyl]-α-(methoxyimino)thiazole-4-acetamide.

EXAMPLE 44

By the general procedure described in Examples 1–4, there is additionally prepared (S,Z)-2-Amino-α-(methoxyimino)-N-[1-[[[[(5-phenyl-3-isothiazolyl)amino]sulfonyl]amino]carbonyl]-2-oxo-3-azetidinyl]thiazole-4-acetamide.

EXAMPLE 45

By the general procedure described in Examples 1–4, there is additionally prepared (S,Z)-2-Amino-N-[1-[[[[(3,4-dimethyl-5-isothiazolyl)amino]sulfonyl]amino]carbonyl]-2-oxo-3-azetidinyl]-α-[1-methylethoxy)imino]thiazole-4-acetamide.

EXAMPLE 46

By the general procedure described in Examples 1–4, there is additionally prepared (S,Z)-2-Amino-α-(ethoxyimino)-N-[1-[[[[5-methyl-3-isothiazolyl)amino]sulfonyl]amino]carbonyl]-2-oxo-3-azetidinyl]thiazole-4-acetamide.

EXAMPLE 47

By the general procedure described in Examples 1–4, there is additionally prepared (S,Z)-2-Amino-α-(methoxyimino)-N-[1-[[[[methyl(5-methyl-3-isothiazolyl)amino]sulfonyl]amino]carbonyl]-2-oxo-3-azetidinyl]-thiazole-4-acetamide.

EXAMPLE 48

By the general procedure described in Examples 1–4, there is additionally prepared (S,Z)-2-Amino-N-[1-[[[[(5-methyl-3-isothiazolyl)amino]sulfonyl]amino]carbonyl]-2-oxo-3-azetidinyl]-α-[(2,2,2-trifluoroethoxy)imino]thiazole-4-acetamide.

EXAMPLE 49

By the general procedure described in Examples 1–4, there is additionally prepared [3S-(3β),(R*)]-α-Hydroxy-N-[1-[[[[(5-methyl-3-isothiazolyl)amino]sulfonyl]amino]carbonyl]-2-oxo-3-azetidinyl]benzeneacetamide.

EXAMPLE 50

By the procedure described in Examples 1–4, there is additionally prepared (S,Z)-5-Amino-α-ethoxyimino-N-[1-[[[[(5-methyl-3-isothiazolyl)amino]carbonyl]-2-oxo-3-azetidinyl]-1,2,4-thiadiazole-3-acetamide.

EXAMPLE 51

By the general procedure described in Example 1, there is prepared (S)-1-[[[[(3-Methyl-5-isothiazolyl)amino]sulfonyl]amino]carbonyl]-2-oxo-3-azetidinyl]-carbamic acid 1,1-dimethylethylester.

EXAMPLE 52

(S,Z)-2-Amino-α-(methoxyimino)-N-[1-[[[[(5-methyl-3-isothiazolyl)amino]sulfonyl]amino]carbonyl]-2-oxo-3-azetidinyl]thiazole-4-acetamide Sodium Salt (Compound A).

| Injectable Dosage Form |
|---|
| Compound A vials contain 250 mg and 500 mg of Compound A. No excipients are added. |

| | 250 mg vial | |
|---|---|---|
| Item | Ingredient | Amount/Vial |
| 1 | Compound A | 250 mg* |

| | 500 mg vial | |
|---|---|---|
| Item | Ingredient | Amount/Vial |
| 1 | Ro 23-4255 | 500 mg* |

Method of Preparation
1. The drug is filled into sterilized vials under aseptic conditions using a powder filling machine such as a Perry Accofil.
2. The filled vials are stoppered with a rubber stopper and sealed with aluminum seals using appropriate equipment.

| Alternate Formulation | | |
|---|---|---|
| | 250 mg vial | |
| Item | Ingredient | Amount/Vial |
| 1 | Compound A | 250 mg* |
| 2 | Lactose, USP | 50 mg |

-continued

| Injectable Dosage Form |
|---|
| Compound A vials contain 250 mg and 500 mg of Compound A. No excipients are added. |

| | | |
|---|---|---|
| 3 | Benzyl Alcohol | 0.3 ml |
| 4 | Water for Injection** | q.s. to 2.0 ml |

| 500 mg vial | | |
|---|---|---|
| Item | Ingredient | Amount/Vial |
| 1 | Compound A | 500 mg* |
| 2 | Lactose, USP | 50 mg |
| 3 | Benzyl Alcohol | 0.3 ml |
| 4 | Water for Injection** | q.s. to 2.0 ml |

Method of Preparation

1. Compound A lactose and benzyl alcohol are dissolved in water for injection and the solution is filtered through a bacterioretentive filter into a sterile container.
2. The solution is subdivided into glass vials under aseptic conditions, the rubber stoppers are positioned and the vials loaded into a lyophilizer and freeze dried using an appropriate cycle.
3. The vials are sealed with aluminum seals under aseptic conditions.

*Additional 6% filling excess is added.
**Removed during lyophilization.

EXAMPLE 56

Minimal Inhibitory Concentrations (μg/mL) values were found for the following compounds

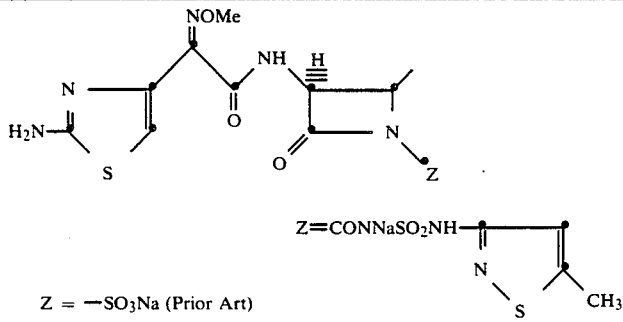

$Z = CONNaSO_2NH$—

| Organisms | Z = —SO₃Na (Prior Art) | |
|---|---|---|
| E. coli 257 | 1 | 0.5 |
| E. coli 48 | 1 | 0.25 |
| K. pneumoniae | 0.5 | 0.5 |
| E. cloacae 9570A | 2 | 0.5 |
| P. vulgaris ATCC 6380 | 2 | 0.063 |
| P. mirabilis 503-1136 | 2 | 0.063 |
| P. mirabilis 190 | 1 | 0.063 |
| S. marcescens SM | 8 | 4 |
| P. aeruginosa Stone 130 | 32 | 64 |
| P. aeruginosa 503-56 | 32 | 128 |
| S. pyogenes 503-782 | 128 | — |
| S. aureus Smith | 64 | >128 |

MIC were obtained in accordance with or the co proceeding.

We claim:

1. A compound of the formula

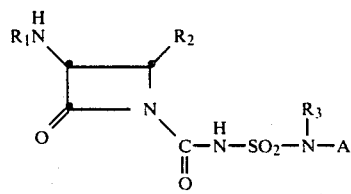

wherein A is

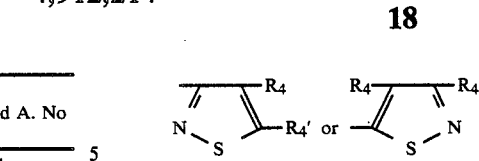

$R_1$ is acyl, $R_2$ is hydrogen, lower alkyl, lower alkoxycarbonyl or aminocarbonyl, $R_3$ is hydrogen or lower alkyl, $R_4$ and $R_4'$ are each hydrogen, lower alkyl, lower alkoxy, aryl, aryloxy or aralkyl, and pharmaceutically acceptable salts thereof.

2. A compound as in claim 1, wherein $R_1$ is selected from the group consisting of 2-(2-chloroacetamido-thiazol-4-yl)-2-methoxyiminoacetyl, 2-(2-aminothiazol-4-yl-2-isopropoxyiminoacetyl, 2-(2-aminothiazol-4-yl)-2-methoxyiminoacetyl, 2-furyl-2-methoxyiminoacetyl, 2-(4-hydroxyphenyl)-2-methoxyiminoacetyl, 2-phenyl-2-methoxyiminoacetyl, 2-phenyl-2-oxyiminoacetyl, 2-thienyl-2-oxyiminoacetyl 2-thienyl-2-(dichloroacetyloxyimino)acetyl, 2-[4-(1D-glutamyloxy)-phenyl]-2-oxyiminoacetyl, 2-[4-(3-amino-3-carboxypropoxy)phenyl]-2-oxyiminoacetyl, 2-(5-chloro-2-chloroacetamidothiazol-4-yl)-2-methoxyiminoacetyl, 2-(5-chloro-2-aminothiazol-4-yl)-2-methoxyiminoacetyl, 2-(5-chloro-2-aminothiazol-4-yl)-2-methoxyiminoacetyl, 2-[1-(t-butoxycarbonyl)isopropoxyimino]-2-(2-sulfoaminothiazol-4-yl)acetyl, 2-[1-(t-butoxycarbonyl)isopropoxyimino]-2-(2-triphenylmethylamino-thiazol-4-acetyl, 2-(2-choroacetamido-thiazol-4-yl)-2-isopropoxyiminoacetyl, 2-methoxyimino-2-(2-sulfoaminothiazol-4-yl)acetyl, 2-[2-(2-chloroacetamidothiazol-4-yl)-2-methoxyiminoacetamido]-2-phenylacetyl, 2-(2-mesylaminothiazol-4-yl)-2-isopropoxyiminoacetyl, 2-(2-imino-3-mesyl-4-thiazolin-4-yl)-2-isopropoxyiminoacetyl, 2-[(2-chloroacetamidothiazol-4-yl-2-[(p-nitrobenzyloxycarbonyl]methoxyimino]acetyl, 2-[(2-aminothiazol-4-yl)2-carboxymethoxyimino]acetyl, and 2-[(2-aminothiazol-4-yl)-2-(1-carboxy-1-methyl-ethoxy-imino)]acetyl.

3. A compound as in claim 1 wherein $R_1$ is of the formula

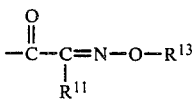

wherein R¹¹ is a carbocylic aromatic group of the formula

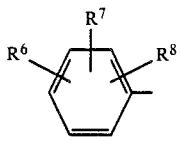

wherein R⁶, R⁷ and R⁸ are each independently hydrogen, halogen, hydroxyl, nitro, amino, cyano, trifluoromethyl, alkyl of from 1 to 4 carbon atoms, alkoxy of from 1 to 4 carbon atoms or aminomethyl, or R¹¹ is a 5-, 6-, or 7-membered heteroaromatic ring containing 1 or 2 hetero atoms selected from among nitrogen, sulfur and oxygen and which is unsubstituted or substituted with halogen, hydroxyl, nitro, cyano, amino, trifluoromethyl, alkyl of from 1 to 4 carbon atoms or alkoxy of from 1 to 4 carbon atoms.

4. A compound as in claim 3 wherein R₁₁ is

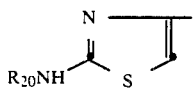

and R₂₀ is hydrogen or an amino protecting group.

5. A compound as in claim 3 wherein R₁₃ is hydrogen, lower alkyl or a group of the formula

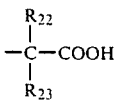

wherein R₂₂ and R₂₃ are selected from the group consisting of hydrogen and lower alkyl or taken together with the carbon atom to which they are attached from C₃–C₇ cycloalkyl.

6. A compound as in claim 5 wherein R₁₁ is

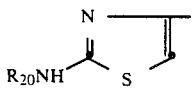

wherein R₂₀ is hydrogen.

7. A compound as in claim 4 wherein R₂, R₃, R₄ and R₄' are each hydrogen or lower alkyl.

8. A compound of claim 7 wherein R₂, R₃, R₄ and R₄' are each hydrogen or methyl.

9. A compound as in claim 8 wherein R₂₀ is hydrogen.

10. A compound as in claim 9 wherein R₁₃ is lower alkyl or a group of the formula

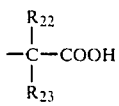

wherein R₂₂ and R₂₃ are each hydrogen or lower alkyl.

11. A compound as in claim 10 wherein R₁₃ is either methyl or a group of the formula

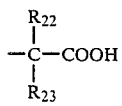

12. A compound as in claim 1 of the formula (S)-N-[1-[[[[(5-lower alkyl-3-isothiazolyl)amino]sulfonyl]amino]carbonyl-2-oxo-3-azetidinyl]benzeneacetamide and its salts.

13. A compound as in claim 12 wherein the lower alkyl group is methyl.

14. A compound as in claim 1 of the formula S-[1-[[[[(5-lower alkyl-3-isothiazolyl)amino]sulfonyl]amino]carbonyl]-2-oxo-3-azetidinyl]carbamic acid phenyl-loweralkyl ester and its salt.

15. A compound as in claim 14 wherein the lower alkyl groups mentioned therein are both methyl.

16. A compound as in claim 1 of the formula (S,Z)-2-amino-α-(loweralkoxyimino)-N-[1-[[[[(5-lower alkyl-3-isothiazolyl)amino]sulfonyl]-amino]carbonyl]-2-oxo-3-azetidinyl]thiazole-4-acetamide and its salt.

17. A compound as in claim 16 wherein the loweralkoxyimino group is methoxyimino and the lower alkyl group is methyl.

18. A compound as in claim 1 of the formula [3S-trans;(Z)]-2-amino-α-(loweralkoxyimino)-N-[4-lower alkyl-1-[[[[(5-lower alkyl-3-isothiazolyl)amino]sulfonyl]amino]carbonyl]-2-oxo-3-azetidinyl]thiazole-4-acetamide and its salt.

19. A compound as in claim 18 wherein both lower alkyl groups thereof are methyl and lower alkoxyimino is methoxyimino.

20. A compound as in claim 1 of the formula 2-[[[1-(2-X-4-thiazolyl)-2-[1-[[[[(5-lower alkyl-3-isothiazolyl)amino]sulfonyl]amino]carbonyl]-2-oxo-3-azetidinyl]amino-2-oxoethylidene]imino]oxy]-2-methylpropanoic acid and its salts wherein X is selected from the group consisting of amino and protected amino.

21. A compound as in claim 20 wherein X is amino.

22. A compound as in claim 1 of the formula 2-[[[1-(2-X-4-thiazolyl)-2-[1-[[[[(5-lower alkyl-3-isothiazolyl)amino]sulfonyl]amino]-2-y-carbonyl]-2-oxo-3-azetidinyl]amino-2-oxoethylidene]imino]oxy](lower alkanoic acid and its salts wherein X is amino or protected amino and y is hydrogen or lower alkyl.

23. A compound as in claim 22 wherein X is amino, the lower alkyl group is methyl y is methyl and the acid moiety is 2-methyl propanoic acid.

24. A compound as in claim 22 wherein X is amino, the lower alkyl group is methyl and y is hydrogen.

25. A compound as in claim 22 wherein y is hydrogen and the lower alkanoic acid group is acetic acid.

26. A compound as defined in claim 1 of the formula 2-[[[1-(2-amino-4-thiazolyl)-2-[1-[[[[(3-R₄'-4-R₄-5-isothiazolyl)amino]sulfonyl]amino]carbonyl]-2-oxo-3-azetidinyl]amino-2-oxoethylidene]imino]oxy]-2-y lower alkanoic acid and its salts wherein y is selected from the group consisting of hydrogen and lower alkyl and R₄ and R₄' are each selected from the group consisting of hydrogen and lower alkyl.

27. A compound as in claim 26 wherein y is methyl the lower alkanoic acid moiety is 2-methyl propanoic acid and R₄' is methyl and R₄ is hydrogen.

28. A compound as in claim 26 wherein $R_4'$ is methyl, $R_4$ is hydrogen, y is hydrogen and the lower alkanoic acid is acetic acid.

29. A compound as in claim 1 of the formula 2-amino(loweralkylimino)-N-[1-[[[[(3-$R_4'$-4-$R_4$-5-isothiazolyl)amino]sulfonyl]amino]carbony]2-oxo-3-azetidinyl]thiazole-4-acetamide and its salts wherein $R_4$ and $R_4'$ are selected from the group consisting of hydrogen and lower alkyl.

30. A compound as in claim 29 wherein the lower alkylimino group is methoxyimino, $R_4'$ is methyl and $R_4$ is hydrogen.

* * * * *

UNITED STATES PATENT AND TRADEMARK OFFICE
CERTIFICATE OF CORRECTION

PATENT NO. : 4,912,214

DATED : March 27, 1990

INVENTOR(S) : Harry A. Albrecht, et al

It is certified that error appears in the above-identified patent and that said Letters Patent is hereby corrected as shown below:

On the title page, item [75] Inventors:

Frederick Martin Konzelman- should be -"Konzelmann"

In claim 2, column 18, lines 24 and 25 delete "2-(5-chloro-2-aminothiazol-4-yl)-2-methoxyiminoacetyl"

Signed and Sealed this

Twenty-fourth Day of September, 1991

*Attest:*

HARRY F. MANBECK, JR.

*Attesting Officer*      *Commissioner of Patents and Trademarks*